United States Patent
McNeil et al.

(10) Patent No.: US 11,967,404 B2
(45) Date of Patent: Apr. 23, 2024

(54) FILTERING ITEMS BASED ON A MEDICAL CONDITION OF AN INDIVIDUAL

(71) Applicant: International Business Machines Corporation, Armonk, NY (US)

(72) Inventors: Kristin E. McNeil, Charlotte, NC (US); Robert Christian Sizemore, Fuquay-Varina, NC (US); Sterling Richardson Smith, Apex, NC (US); David Blake Werts, Charlotte, NC (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 755 days.

(21) Appl. No.: 16/564,192

(22) Filed: Sep. 9, 2019

(65) Prior Publication Data
US 2021/0074392 A1 Mar. 11, 2021

(51) Int. Cl.
*G16H 10/60* (2018.01)
*G06N 20/00* (2019.01)

(52) U.S. Cl.
CPC ............. *G16H 10/60* (2018.01); *G06N 20/00* (2019.01)

(58) Field of Classification Search
CPC ............................... G16H 10/60; G06N 20/00
See application file for complete search history.

(56) References Cited

U.S. PATENT DOCUMENTS

| 11,017,892 B1 * | 5/2021 | Knas ...................... G16H 20/10 |
| 2010/0280895 A1 | 11/2010 | Mottola |
| 2014/0089006 A1 | 3/2014 | Abreu |
| 2014/0289220 A1 | 9/2014 | Gottfurcht et al. |
| 2015/0132722 A1 * | 5/2015 | Menczel ............... A61B 5/1118 434/127 |
| 2016/0358279 A1 * | 12/2016 | Ghouri ................... G16H 15/00 |
| 2017/0091419 A1 | 3/2017 | Hoglund et al. |
| 2019/0228856 A1 * | 7/2019 | Leifer ................. G06F 16/9035 |
| 2019/0340906 A1 * | 11/2019 | Williams ........... G08B 21/0277 |

* cited by examiner

*Primary Examiner* — Jay M. Patel
(74) *Attorney, Agent, or Firm* — CANTOR COLBURN LLP; Kelsey M. Skodje (57) ABSTRACT

Aspects of the present disclosure provide a computer-implemented method that includes obtaining the medical condition of the individual based at least in part on a personal identifier associated with the individual, the medical condition being determined by performing natural language processing of medical information associated with the individual. The method further includes obtaining characteristics of the plurality of items. The method further includes comparing the characteristics of the plurality of items to a restriction associated with the medical condition of the individual. The method further includes, responsive to determining that at least one of the characteristics of the plurality of items violates the restriction associated with the medical condition of the individual, preventing the individual from obtaining the item of the plurality of items associated with the violation.

20 Claims, 7 Drawing Sheets

FILTERING ITEMS BASED ON A MEDICAL CONDITION OF AN INDIVIDUAL

BACKGROUND

The present invention generally relates to natural language processing, and more specifically, to the filtering of items based on a medical condition of an individual.

Individuals with certain medical conditions may wish or need to avoid certain items. For example, an individual with a peanut allergy may wish or need to avoid items with peanuts. Similarly, an individual with high blood pressure may wish or need to avoid items with a threshold amount of sodium. In some situations, individuals with medical conditions may wish or need to obtain certain items. For example, an individual with iron-deficiency anemia may wish or need to obtain items that have a certain amount of iron.

SUMMARY

Embodiments of the present invention are directed to filtering items based on a medical condition of an individual.

A non-limiting example computer-implemented method includes obtaining the medical condition of the individual based at least in part on a personal identifier associated with the individual, the medical condition being determined by performing natural language processing of medical information associated with the individual. The method further includes obtaining characteristics of the plurality of items. The method further includes comparing the characteristics of the plurality of items to a restriction associated with the medical condition of the individual. The method further includes, responsive to determining that at least one of the characteristics of the plurality of items violates the restriction associated with the medical condition of the individual, preventing the individual from obtaining the item of the plurality of items associated with the violation.

Another embodiment of the present invention implement features of the above-described method in a computer system. The system includes a memory comprising computer readable instructions. The system further includes a processing device for executing the computer readable instructions, the computer readable instructions controlling the processing device to perform operations. The operations include obtaining the medical condition of the individual based at least in part on a personal identifier associated with the individual, the medical condition being determined by performing natural language processing of medical information associated with the individual. The operations further include obtaining characteristics of the plurality of items. The operations further include comparing the characteristics of the plurality of items to a restriction associated with the medical condition of the individual. The operations further include, responsive to determining that at least one of the characteristics of the plurality of items violates the restriction associated with the medical condition of the individual, preventing the individual from obtaining the item of the plurality of items associated with the violation.

Another embodiment of the present invention implement features of the above-described method in computer program product. The computer program product includes a computer readable storage medium having program instructions embodied therewith, the program instructions executable by a processor to cause the processor to perform operations. The operations include obtaining the medical condition of the individual based at least in part on a personal identifier associated with the individual, the medical condition being determined by performing natural language processing of medical information associated with the individual. The operations further include obtaining characteristics of the plurality of items. The operations further include comparing the characteristics of the plurality of items to a restriction associated with the medical condition of the individual. The operations further include, responsive to determining that at least one of the characteristics of the plurality of items violates the restriction associated with the medical condition of the individual, preventing the individual from obtaining the item of the plurality of items associated with the violation.

The embodiments described herein are less time-consuming and error-prone than conventional manual inspection approaches. The present techniques use natural language processing to determine medical conditions and then, based on the medical conditions, item acquisition is restricted or an alert that an item matches a restriction is issued. Accordingly, when it is determined that at least one of the characteristics of the plurality of items violates the restriction associated with the medical condition of the individual, the individual is prevented from obtaining the item associated with the violation.

In addition to one or more of the features described above, or as an alternative to any of the foregoing embodiments, one or more of the method, system, and computer program product can include, responsive to determining that at least one of the characteristics of the plurality of items violates the one or more restrictions associated with the medical condition of the individual, notifying the individual of the violation. Notifying the individual of the violation informs the individual that the item should not be purchased, enabling the individual to select an alternate item or to not purchase the item.

In addition to one or more of the features described above, or as an alternative to any of the foregoing embodiments, one or more of the method, system, and computer program product can include, responsive to determining that at least one of the characteristics of the plurality of items violates the one or more restrictions associated with the medical condition of the individual, recommending a substitute item in lieu of the item associated with the violation. Recommending the substitute item enables the individual not purchase the item associated with the restriction and instead purchase a substitute item that is not associated with a restriction.

In addition to one or more of the features described above, or as an alternative to any of the foregoing embodiments, the personal identifier associated with the individual is received from a form of payment associated with the individual. Using a form of payment associated with the individual enables existing forms of payment to be used to identify the user, eliminating the need for a dedicated identifier.

In addition to one or more of the features described above, or as an alternative to any of the foregoing embodiments, the personal identifier associated with the individual is received from a loyalty card associated with the individual. Using a loyalty card associated with the individual enables existing loyalty cards to be used to identify the user, eliminating the need for a dedicated identifier.

In addition to one or more of the features described above, or as an alternative to any of the foregoing embodiments, one or more of the method, system, and computer program product can include, prior to obtaining the characteristics of the plurality of items, receiving an identification of each of the plurality of items, wherein obtaining the characteristics is based at least in part on the identification of each of the plurality of items; and prior to obtaining the medical condition of the individual, receiving, by the processing device, the personal identifier associated with the individual.

In addition to one or more of the features described above, or as an alternative to any of the foregoing embodiments, one or more of the method, system, and computer program product can include, the natural language processing is rule-based natural language processing. Rule-based natural language processing offers high recall, sequence labeling, pattern identification, and other benefits.

In addition to one or more of the features described above, or as an alternative to any of the foregoing embodiments, one or more of the method, system, and computer program product can include, wherein the natural language processing is machine learning-based natural language processing. Machine learning-based natural language processing offers improved completeness, higher efficiency, unsupervised learning, multiple levels of representation, and other benefits.

Additional technical features and benefits are realized through the techniques of the present invention. Embodiments and aspects of the invention are described in detail herein and are considered a part of the claimed subject matter. For a better understanding, refer to the detailed description and to the drawings.

BRIEF DESCRIPTION OF THE DRAWINGS

The specifics of the exclusive rights described herein are particularly pointed out and distinctly claimed in the claims at the conclusion of the specification. The foregoing and other features and advantages of the embodiments of the invention are apparent from the following detailed description taken in conjunction with the accompanying drawings in which:

The diagrams depicted herein are illustrative. There can be many variations to the diagram or the operations described therein without departing from the scope of the invention. For instance, the actions can be performed in a differing order or actions can be added, deleted or modified. Also, the term "coupled" and variations thereof describes having a communications path between two elements and does not imply a direct connection between the elements with no intervening elements/connections between them. All of these variations are considered a part of the specification.

DETAILED DESCRIPTION

One or more embodiments of the present invention provide item filtering based on a medical condition of an individual. When an individual goes shopping, such as at a physical store or in an e-commerce application or web portal, the user may desire to purchase an item. However, in some cases, the desired item may conflict with a medical condition of the user. As an example, a user with nut allergies desiring to purchase a certain protein bar may be unaware that the item contains nuts. To detect this, the user must manually inspect the item packaging, such as by reading an ingredient list. This process is time-consuming and error-prone (e.g., the individual misses a restricted ingredient on the ingredient list, the individual forgets about a certain restriction, an ingredient changes on a product familiar to the user and the use is unaware of the change etc.).

The embodiments described herein address the shortcomings of the prior art by using natural language processing to determine medical conditions for an individual based on the individual's medical data. Restrictions are determined from the medical conditions and are compared against characteristic (e.g., ingredients) of items. Where matches are detected, the present techniques take action, such as by preventing the individual from acquiring the item having a match to a restriction.

One or more embodiments of the present invention provide technological improvements over current methods of monitoring items for acquisition that require individuals to manually inspect items and mentally compare characteristics of such items against known restrictions. Disadvantages of contemporary approaches may include being time-consuming and error-prone, as discussed herein. One or more embodiments of the present invention provide technical solutions to one or more of these disadvantages of existing solutions by using natural language processing to determine medical conditions and then, based on the medical conditions, restricting item acquisition or alerting that an item matches a restriction.

Figure 1:
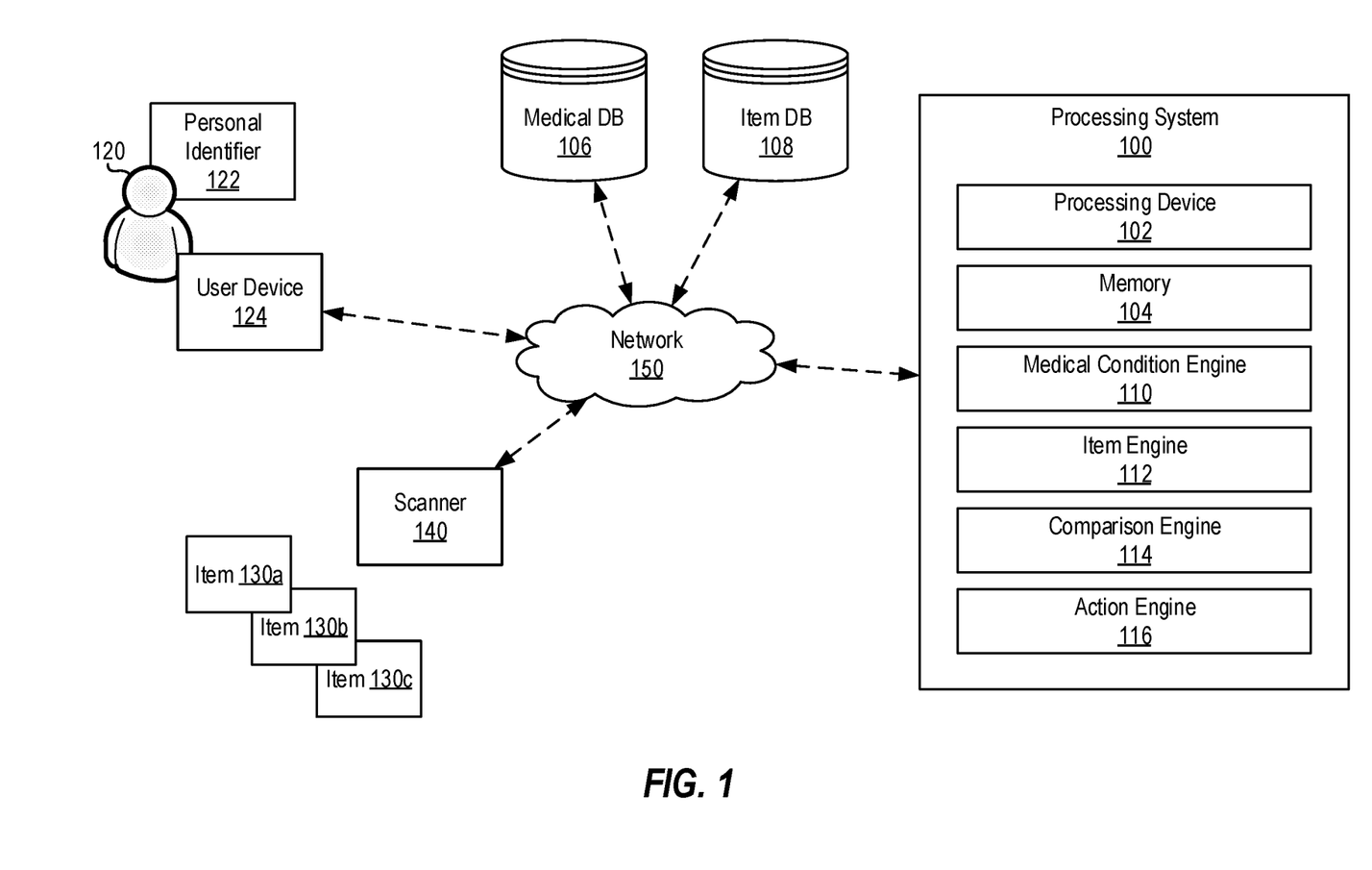
FIG. 1 depicts a block diagram of a processing system for filtering items based on a medical condition of an individual according to one or more embodiments described herein.

Turning now to FIG. 1, depicted is a block diagram of a processing system 100 for filtering items based on a medical condition of an individual 120 according to one or more embodiments described herein. The processing system 100 filters items 130a, 130b, 130c (collectively referred to herein as the "items 130") based on a medical condition of the individual 120 by obtaining the medical condition using a personal identifier 122 associated with the individual 120, obtaining characteristics of the items 130, comparing the characteristics of the items 130 to a restriction associated with the medical condition of the individual 120. Then, responsive to determining that at least one of the characteristics of the items 130 violates the restriction associated with the medical condition of the individual 120, the individual 120 is prevented from obtaining the item of the items 130 associated with the violation.

The processing system 100 includes a processing device 102, a memory 104, a medical condition engine 110, an item engine 112, a comparison engine 114, and an action engine 116.

As an example, the individual 120 is shopping for the items 130, such as online via an e-commerce platform or in a physical store. The individual 120 collects the items 130 and proceeds to check out. The items 130 are scanned by a scanner 140, which can be an optical scanner, laser scanner, etc. In an example, the scanner 140 is a barcode scanner. In another example, the scanner 140 is a camera associated with a processing system configured to perform image recognition to recognize the items 130.

Once scanned, the item engine 112 obtains characteristics about the items 130. Examples of characteristics include a product identifier, ingredients, serving sizes, nutritional information, manufacturing date, expiration date, and other information. The characteristics are stored in and retrieved from a suitable data repository, such as the item database 108. The individual 120 provides a personal identifier 122 to identify the individual 120. In examples, the personal identifier 122 can be a government-issued identification card, a form of payment (e.g., a debit card, a credit card, a check, etc.) associated with the individual 120, a username and passcode, a loyalty card (i.e., a store rewards card) or other suitable identifying information. The medical condition engine 110 obtains a medical condition associated with the individual 120 based on the personal identifier 122.

The medical condition engine 110 performs natural language processing of medical information stored in a medical database 106 (or another suitable data repository) to determine the medical condition. In some examples, the individual 120 can input a medical condition and/or a restriction manually. For example, if the individual 120 is on a low-carbohydrate diet, the individual 120 can manually set a restriction to prevent the individual 120 from purchasing foods high in carbohydrates. The comparison engine 114 then compares the characteristics of the items 130 to a restriction associated with the medical condition of the individual 120. If it is determined that the characteristics of one of the items 130 matches a restriction associated with the medical condition of the individual 120, the action engine 116 can prevent the individual 120 from purchasing the item, can issue a warning/notification to the individual 120, can alert another individual, can suggest an alternate or substitute item, etc.

In another example, the individual 120 uses the user device 124 and/or the scanner 140 to read or scan the personal identifier 122 prior to selecting any of the items 130. The processing system 100 identifies the individual 120 and obtains a medical condition of the individual 120 using the personal identifier 122 associated with the individual 120. As in the example above, the medical condition engine 110 determines the medical condition of the individual 120 by performing natural language processing of medical information associated with the individual 120, such as the information stored in the medical database 106 or other medical information.

The individual 120 then selects items 130, such as in an e-commerce application or web portal on the user device 124 or by scanning items in a store using the scanner 140. The item engine 112 obtains characteristics of the items 130. The comparison engine 114 then compares the characteristics of the items 130 to a restriction associated with the medical condition of the individual 120. If it is determined that the characteristics of one of the items 130 matches a restriction associated with the medical condition of the individual 120, the action engine 116 can prevent the individual 120 from purchasing the item, can issue a warning/notification to the individual 120, can alert another individual, can suggest an alternate item, etc.

The processing system 100 can include a network adapter (e.g., the network adapter 726 of FIG. 7) to transmit data to and receive data from other devices, including, for example, one or more of the user device 124, the scanner 140, the medical database 106, and the item database 108. The processing system 100 can transmit data to and receive data from other devices directly and/or via a network 150. The network 150 represents any one or a combination of different types of suitable communications networks such as, for example, cable networks, public networks (e.g., the Internet), private networks, wireless networks, cellular networks, or any other suitable private and/or public networks. Further, the network 150 may have any suitable communication range associated therewith and may include, for example, global networks (e.g., the Internet), metropolitan area networks (MANs), wide area networks (WANs), local area networks (LANs), or personal area networks (PANs). In addition, the network 150 can include any type of medium over which network traffic may be carried including, but not limited to, coaxial cable, twisted-pair wire, optical fiber, a hybrid fiber coaxial (HFC) medium, microwave terrestrial transceivers, radio frequency communication mediums, satellite communication mediums, or any combination thereof.

The various components, modules, engines, etc. described regarding FIG. 1 can be implemented as instructions stored on a computer-readable storage medium, as hardware modules, as special-purpose hardware (e.g., application specific hardware, application specific integrated circuits (ASICs), application specific special processors (ASSPs), field programmable gate arrays (FPGAs), as embedded controllers, hardwired circuitry, etc.), or as some combination or combinations of these. According to aspects of the present disclosure, the engine(s) described herein can be a combination of hardware and programming. The programming can be processor executable instructions stored on a tangible memory, and the hardware can include the processing device 102 for executing those instructions. Thus a system memory (e.g., memory 104) can store program instructions that when executed by the processing device 102 implement the engines described herein. Other engines can also be utilized to include other features and functionality described in other examples herein. The features and functionality of the processing system 100, and the additional components depicted in FIG. 1, are now described with respect to FIG. 2.

Figure 2:
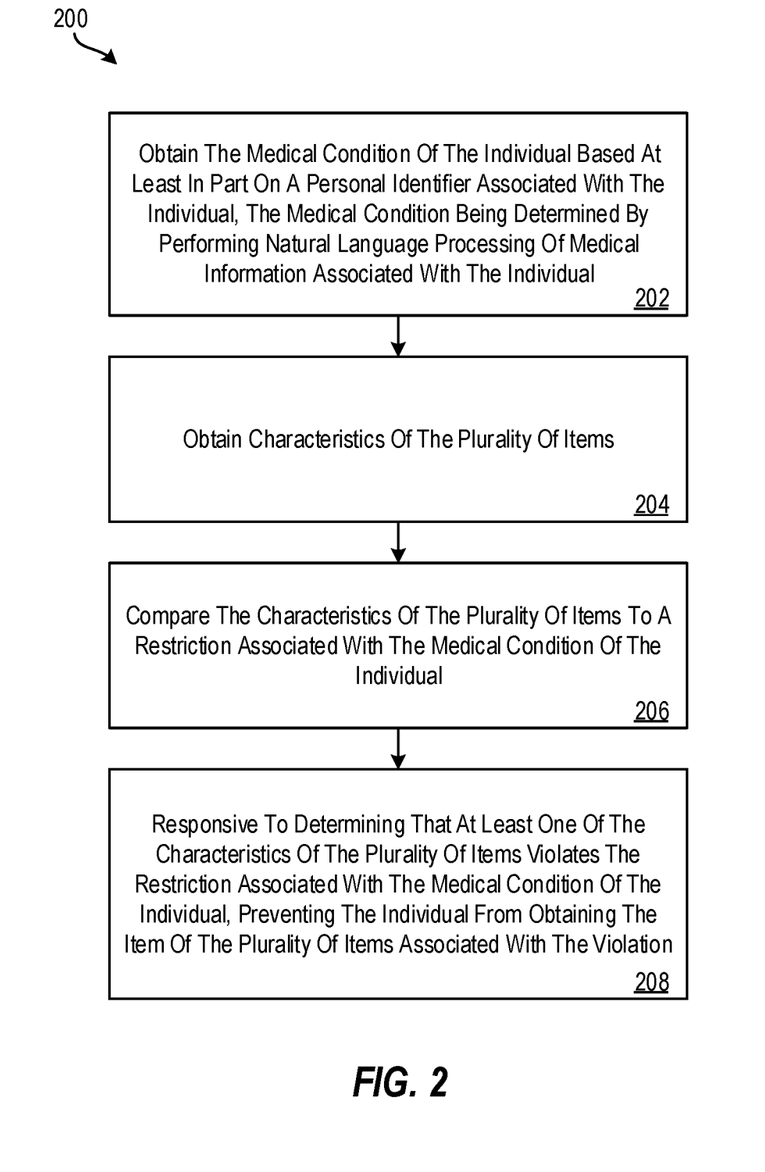
FIG. 2 depicts a flow diagram of a method for filtering items based on a medical condition of an individual according to one or more embodiments described herein.

FIG. 2 depicts a flow diagram of a method 200 for filtering items based on a medical condition of an individual according to one or more embodiments described herein. The method 200 can be implemented by any suitable processing system (e.g., the processing system 100 of FIG. 1, the processing system 700 of FIG. 7, a cloud computing node 10 of the cloud computing environment 50 of FIG. 5, etc.), processing device (e.g., the processing device 102 of FIG. 1, the processor(s) 721 of FIG. 7, etc.), or the like.

At block 202, the medical condition engine 110 obtains the medical condition of the individual 120 based at least in part on the personal identifier 122 associated with the individual 120. Such medical information can be stored in the medical database 106 or another suitable repository (or repositories) for storing such information.

As an example, medical information states that the individual 120 had high blood pressure during the past several doctor visits. Doctor-provided notes from these visits state "patient should avoid foods with high sodium." The medical condition engine 110 accordingly determine a medical condition of "high blood pressure."

As another example, medical information can state that the individual 120 has a known peanut allergy. The medical condition engine 110 accordingly determine a medical condition of "peanut allergy."

The medical condition engine 110 determines the medical condition by performing natural language processing of medical information associated with the individual 120. Natural language processing (NLP) can be rule-based NLP, machine learning-based NLP, and/or a hybrid of rule-based NLP and machine learning-based NLP. As an example, a unified medical language (or ontology) can be applied using a rule-based NLP technique. In such an example, the unified medical language is used to identify the medical condition from the medical information.

In the case of machine learning-based NLP, a neural network can be trained to determine medical conditions from medical information. More specifically, the present techniques can incorporate and utilize rule-based decision making and artificial intelligence (AI) reasoning to accomplish the various operations described herein, namely determining medical conditions from medical information. The phrase "machine learning" broadly describes a function of electronic systems that learn from data. A machine learning system, engine, or module can include a trainable machine learning algorithm that can be trained, such as in an external cloud environment, to learn functional relationships between inputs and outputs that are currently unknown, and the resulting model can be used to determine medical conditions. In one or more embodiments, machine learning functionality can be implemented using an artificial neural network (ANN) having the capability to be trained to perform a currently unknown function. In machine learning and cognitive science, ANNs are a family of statistical learning models inspired by the biological neural networks of animals, and in particular the brain. ANNs can be used to estimate or approximate systems and functions that depend on a large number of inputs. Convolutional neural networks (CNN) are a class of deep, feed-forward ANN that are particularly useful at analyzing visual imagery.

ANNs can be embodied as so-called "neuromorphic" systems of interconnected processor elements that act as simulated "neurons" and exchange "messages" between each other in the form of electronic signals. Similar to the so-called "plasticity" of synaptic neurotransmitter connections that carry messages between biological neurons, the connections in ANNs that carry electronic messages between simulated neurons are provided with numeric weights that correspond to the strength or weakness of a given connection. The weights can be adjusted and tuned based on experience, making ANNs adaptive to inputs and capable of learning. For example, an ANN for handwriting recognition is defined by a set of input neurons that can be activated by the pixels of an input image. After being weighted and transformed by a function determined by the network's designer, the activation of these input neurons are then passed to other downstream neurons, which are often referred to as "hidden" neurons. This process is repeated until an output neuron is activated. The activated output neuron determines which character was read. It should be appreciated that these same techniques can be applied in the case of determining medical conditions for an individual based on the medical information associated with that individual.

At block 204, the item engine 112 obtains characteristics of the plurality of items 130. The characteristics are stored, for example, in the item database 108 or another suitable repository (or repositories) for storing such information. Item characteristics can include ingredients or other elemental aspects of the item. For example, if the item is a foodstuff, the characteristics for the item are a list of ingredients in the item. As an additional example, if the item is a foodstuff, the characteristics can include nutritional information about the item, such as calorie information, serving size information, nutrient composition information, and the like.

At block 206, the comparison engine 114 compares the characteristics of the plurality of items 130 to a restriction associated with the medical condition of the individual 120. The restriction is determined, such as by the medical condition engine 110, to identify a restriction based on the medical condition of the individual 120.

Using the described example in which the individual 120 has a medical condition of "high blood pressure," the restriction may be "no food with more than 140 mg of sodium." For the described example in which the individual 120 has a medical condition of "peanut allergy," the restriction may be "no food made with nuts." In some examples, the restriction can be based on the severity of the medical condition. For example, if the individual 120 is highly allergic to peanuts, the restriction might be "avoid any food made with nuts or prepared an area that may contain nuts." As another example, if the individual 120 has a mild peanut allergy, the restriction may be "avoid foods with the top three ingredients by amount including peanuts."

In some examples, the individual 120 is presented with the restriction(s), such as by displaying the restriction(s) on a display of the user device 124. The individual 120 can rank the restrictions, alter the restrictions, reject the restrictions, and the like. For example, the individual 120 can rank a "peanut allergy" restriction to be low if the individual 120 is only mildly allergic to peanuts. The individual 120 can also input restrictions manually. For example, if the individual 120 is on a low-carbohydrate diet, the individual 120 can manually set a restriction to prevent the individual 120 from purchasing foods high in carbohydrates.

At block 208, the action engine 116, responsive determining that at least one of the characteristics of the plurality of items 130 violates restriction associated with the medical condition of the individual 120, preventing the individual 120 from obtaining the item of the plurality of items 130 associated with the violation. The action engine 116 can take other actions as well, such as alerting the individual 120 of the match between the item and the restriction. For example, if the individual 120 has a mild peanut allergy, the action engine 116 might warn the individual 120 by displaying a notification on the user device 124, while if the individual 120 has a severe peanut allergy, the action engine 116 might prevent the individual 120 from purchasing the item altogether. The action engine 116 can also recommend an alternate item.

Additional processes also may be included. In some examples, prior to obtaining the characteristics of the plurality of items, the item engine 112 receives an identification of each of the plurality of items. Identification of an item can be scanning (such as using the scanner 140) a universal product code (UPC) associated with the item. The item engine 112 then obtains the characteristics of the item based at least in part on the identification (e.g., the UPC) of each of the plurality of items. The method 200 further includes, in an example, prior to obtaining the medical condition of the individual, the processing system 100 receives the personal identifier associated with the individual. It should be understood that the process depicted in FIG. 2 represents an illustration, and that other processes may be added or existing processes may be removed, modified, or rearranged without departing from the scope of the present disclosure.

Figure 3:
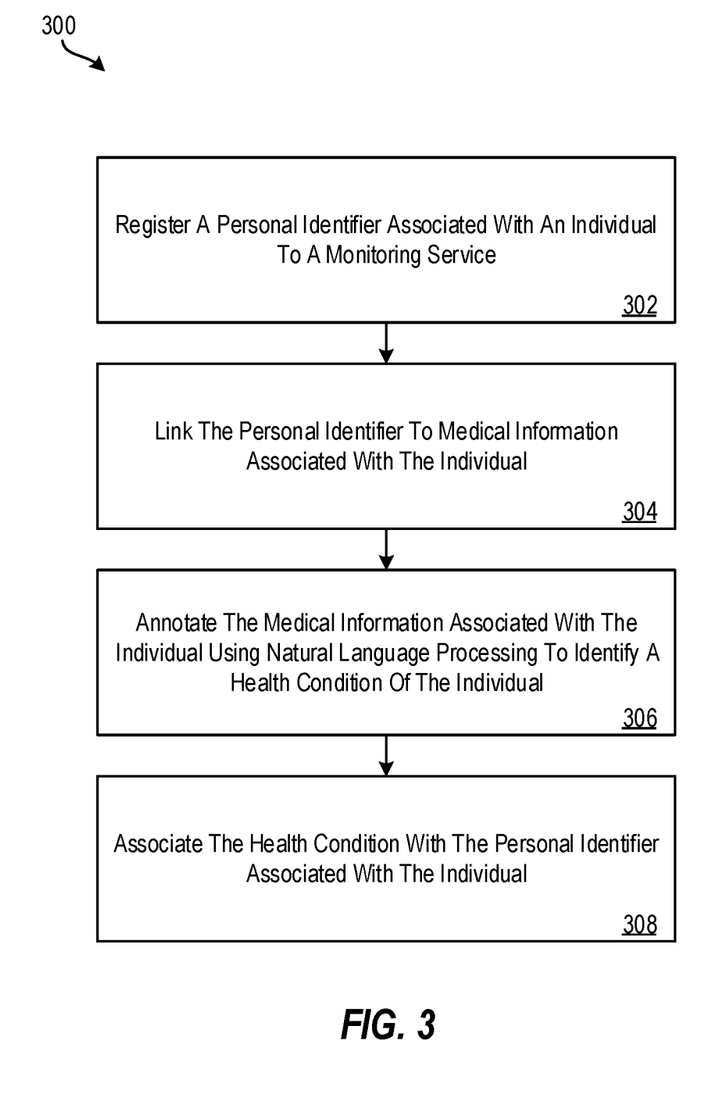
FIG. 3 depicts a flow diagram of a method for associating a personal identifier of an individual with a medical condition of the individual according to one or more embodiments described herein

FIG. 3 depicts a flow diagram of a method 300 for associating a personal identifier of an individual with a medical condition of the individual according to one or more embodiments described herein. The method 300 can be implemented by any suitable processing system (e.g., the processing system 100 of FIG. 1, the processing system 700 of FIG. 7, a cloud computing node 10 of the cloud computing environment 50 of FIG. 5, etc.), processing device (e.g., the processing device 102 of FIG. 1, the processor(s) 721 of FIG. 7, etc.), or the like.

At block 302, the individual 120 registers the personal identifier 122 to a monitoring service (e.g., the processing system 100). The individual can access the processing system 100, for example, using the user device 124. The user device 124 can be any suitable type of computer processing system, such as a smartphone, laptop computer, desktop computer, tablet computer, wearable electric device, and the like. As an example, the user device 124 executes an application that presents a user interface to the individual 120 on a display (not shown) of the user device 124. The individual can then input information, such a number, code, or other identifier associated with the personal identifier 122 as well as information about the individual 120 (e.g., name, address, medical information, etc.).

At block 304, the medical condition engine 110 links the personal identifier 122 to medical information associated with the individual 120. For example, a name associated with the personal identifier is matched to and linked with a name in the medical database 106. At block 306, the medical condition engine 110 annotate the medical information (e.g., the medical information stored in the medical database 106) associated with the individual 120 using natural language processing to identify a health condition of the individual 120. At block 308, the medical condition engine 110 associates the health condition with the personal identifier 122 associated with the individual 120. This enables the personal identifier 122 associated with the individual 120 to be used to retrieve medical information about the individual 120.

Additional processes also may be included, and it should be understood that the process depicted in FIG. 3 represents an illustration, and that other processes may be added or existing processes may be removed, modified, or rearranged without departing from the scope of the present disclosure.

Figure 4:
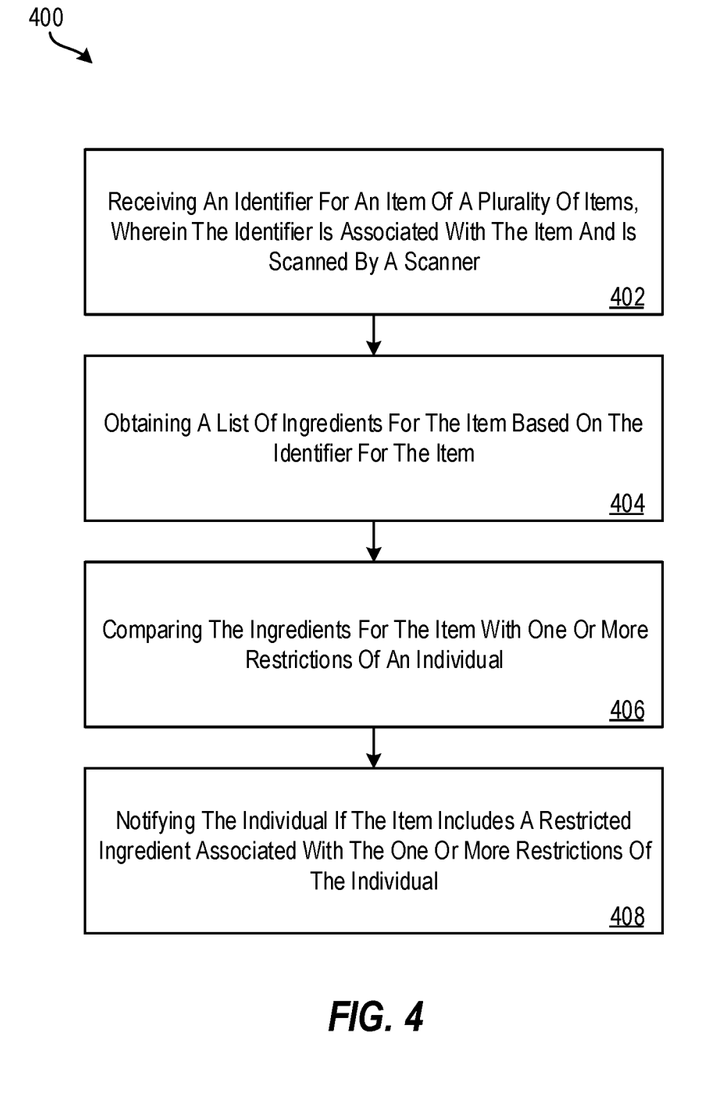
FIG. 4 depicts a flow diagram of a method filtering items based on a medical condition of an individual and ingredients of the items according to one or more embodiments described herein.

FIG. 4 depicts a flow diagram of a method 400 filtering items based on a medical condition of an individual and ingredients of the item according to one or more embodiments described herein. The method 400 can be implemented by any suitable processing system (e.g., the processing system 100 of FIG. 1, the processing system 700 of FIG. 7, a cloud computing node 10 of the cloud computing environment 50 of FIG. 5, etc.), processing device (e.g., the processing device 102 of FIG. 1, the processor(s) 721 of FIG. 7, etc.), or the like.

At block 402, the item engine 112 receives an identifier for an item (e.g., one of the items 130a, 130b, 130c) of a plurality of items 130. The identifier is associated with the item and is scanned by the scanner 140, which can be an optical scanner, laser scanner, etc. In an example, the scanner 140 is a barcode scanner and scans a universal product code (UPC) on or associated with the item.

At block 404, the item engine 112 obtains a list of ingredients for the item based on the identifier for the item. The list of ingredients is stored in a database, such as the item database 108. Ingredient lists for items can be provided by an agency, such as the Food and Drug Administration, by manufactures of the items, by third-parties, or by other sources.

At block 406, the comparison engine 114 compares the ingredients for the item with one or more restrictions of an individual. The restrictions are determined by performing natural language processing on medical records of the individual.

At block 408, notifying the individual 120 if the item (e.g., one of the items 130) includes a restricted ingredient associated with the one or more restrictions of the individual. For example, a message can be sent to the user device 124 to alert the individual 120 that the item includes a restricted ingredient. This may be particularly useful when an ingredient is not listed on the package of the item, for example. The individual can then select an alternate item or can choose not to select that item. In some examples, the individual is prevented from acquiring the item. For example, the individual's form of payment is declined, thus preventing the individual 120 from acquiring the item.

Additional processes also may be included, and it should be understood that the process depicted in FIG. 4 represents an illustration, and that other processes may be added or existing processes may be removed, modified, or rearranged without departing from the scope of the present disclosure.

Example embodiments of the disclosure include or yield various technical features, technical effects, and/or improvements to technology. Example embodiments of the disclosure provide monitoring system configured to determine a medical condition for an individual by performing natural language processing on medical information associated with the user, compare characteristics of items to a restriction associated with the medical condition of the individual, and then take an action such as preventing the individual from acquiring the item. These aspects of the disclosure constitute technical features that yield the technical effect of determining medical conditions of an individual using NLP, which prevents the individual from having to manually enter restrictions (e.g., nut allergy, low carbohydrate food, etc.). These aspects also provide the technical effect of updating medical conditions as medical information for the user changes (e.g., if medical information changes, new medical conditions can be identified using NLP techniques as described herein and can be used to monitor the individual's attempted acquisition of items). As a result of these technical features and technical effects, a monitoring system in accordance with example embodiments of the disclosure represents an improvement to existing monitoring techniques. It should be appreciated that the above examples of technical features, technical effects, and improvements to technology of example embodiments of the disclosure are merely illustrative and not exhaustive.

It is to be understood that, although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 5:
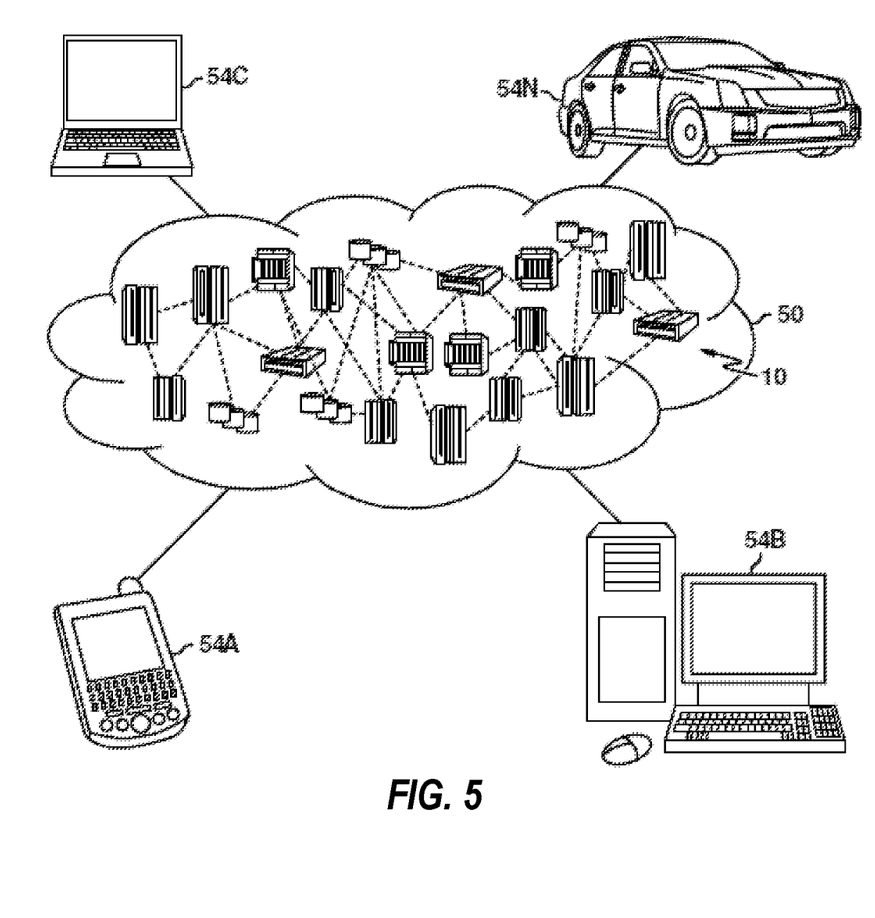
FIG. 5 depicts a cloud computing environment according to one or more embodiments described herein.

Referring now to FIG. 5, illustrative cloud computing environment 50 is depicted. As shown, cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 5 are intended to be illustrative only and that computing nodes 10 and cloud computing environment 50 can communicate with any type of computerized device over any type of network and/or network addressable connection (e.g., using a web browser).

Figure 6:
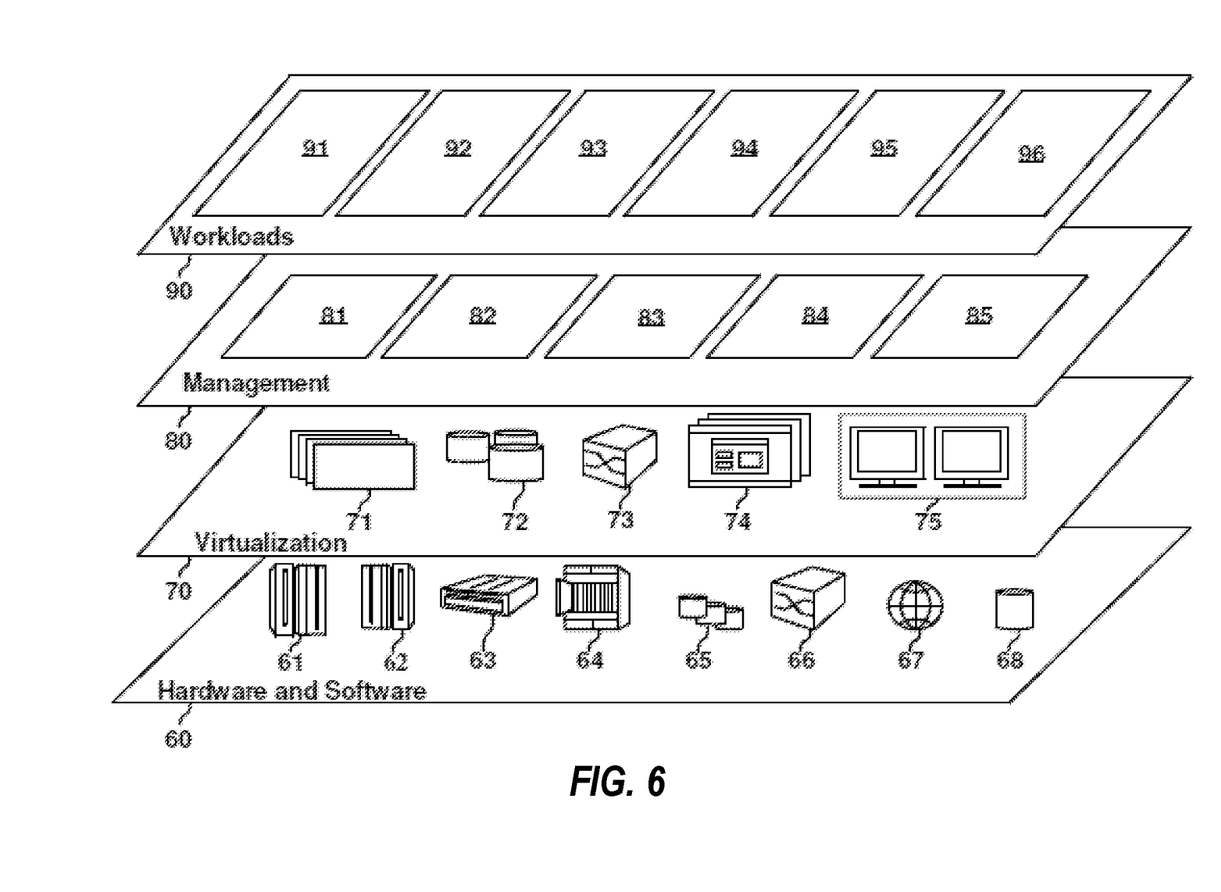
FIG. 6 depicts abstraction model layers according to one or more embodiments described herein.

Referring now to FIG. 6, a set of functional abstraction layers provided by cloud computing environment 50 (FIG. 5) is shown. It should be understood in advance that the components, layers, and functions shown in FIG. 6 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and filtering items based on a medical condition of an individual 96.

Figure 7:
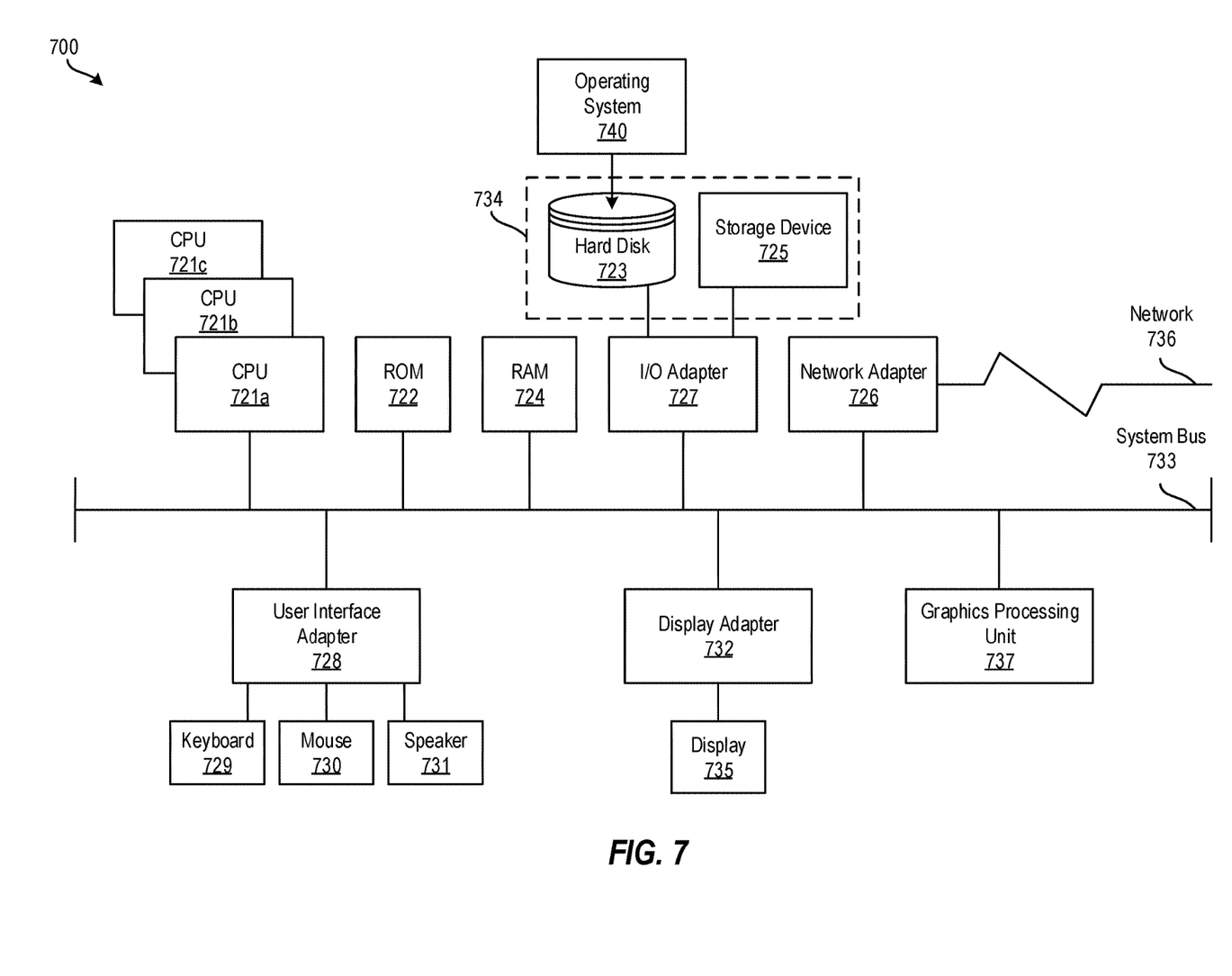
FIG. 7 depicts a block diagram of a processing system for implementing the presently described techniques according to one or more embodiments described herein.

It is understood that one or more embodiments described herein is capable of being implemented in conjunction with any other type of computing environment now known or later developed. For example, FIG. 7 depicts a block diagram of a processing system 700 for implementing the techniques described herein. In accordance with one or more embodiments described herein, the processing system 700 is an example of a cloud computing node 10 of FIG. 5. In examples, processing system 700 has one or more central processing units ("processors" or "processing resources") 721a, 721b, 721c, etc. (collectively or generically referred to as processor(s) 721 and/or as processing device(s)). In aspects of the present disclosure, each processor 721 can include a reduced instruction set computer (RISC) microprocessor. Processors 721 are coupled to system memory (e.g., random access memory (RAM) 724) and various other components via a system bus 733. Read only memory (ROM) 722 is coupled to system bus 733 and may include a basic input/output system (BIOS), which controls certain basic functions of processing system 700.

Further depicted are an input/output (I/O) adapter 727 and a network adapter 726 coupled to system bus 733. I/O adapter 727 may be a small computer system interface (SCSI) adapter that communicates with a hard disk 723 and/or a storage device 725 or any other similar component. I/O adapter 727, hard disk 723, and storage device 725 are collectively referred to herein as mass storage 734. Operating system 740 for execution on processing system 700 may be stored in mass storage 734. The network adapter 726 interconnects system bus 733 with an outside network 736 enabling processing system 700 to communicate with other such systems.

A display (e.g., a display monitor) 735 is connected to system bus 733 by display adapter 732, which may include a graphics adapter to improve the performance of graphics intensive applications and a video controller. In one aspect of the present disclosure, adapters 726, 727, and/or 732 may be connected to one or more I/O busses that are connected to system bus 733 via an intermediate bus bridge (not shown). Suitable I/O buses for connecting peripheral devices such as hard disk controllers, network adapters, and graphics adapters typically include common protocols, such as the Peripheral Component Interconnect (PCI). Additional input/output devices are shown as connected to system bus 733 via user interface adapter 728 and display adapter 732. A keyboard 729, mouse 730, and speaker 731 may be interconnected to system bus 733 via user interface adapter 728, which may include, for example, a Super I/O chip integrating multiple device adapters into a single integrated circuit.

In some aspects of the present disclosure, processing system 700 includes a graphics processing unit 737. Graphics processing unit 737 is a specialized electronic circuit designed to manipulate and alter memory to accelerate the creation of images in a frame buffer intended for output to a display. In general, graphics processing unit 737 is very efficient at manipulating computer graphics and image processing, and has a highly parallel structure that makes it more effective than general-purpose CPUs for algorithms where processing of large blocks of data is done in parallel.

Thus, as configured herein, processing system 700 includes processing capability in the form of processors 721, storage capability including system memory (e.g., RAM 724), and mass storage 734, input means such as keyboard 729 and mouse 730, and output capability including speaker 731 and display 735. In some aspects of the present disclosure, a portion of system memory (e.g., RAM 724) and mass storage 734 collectively store the operating system 740 such as the AIX® operating system from IBM Corporation to coordinate the functions of the various components shown in processing system 700.

Various embodiments of the invention are described herein with reference to the related drawings. Alternative embodiments of the invention can be devised without departing from the scope of this invention. Various connections and positional relationships (e.g., over, below, adjacent, etc.) are set forth between elements in the following description and in the drawings. These connections and/or positional relationships, unless specified otherwise, can be direct or indirect, and the present invention is not intended to be limiting in this respect. Accordingly, a coupling of entities can refer to either a direct or an indirect coupling, and a positional relationship between entities can be a direct or indirect positional relationship. Moreover, the various tasks and process steps described herein can be incorporated into a more comprehensive procedure or process having additional steps or functionality not described in detail herein.

The following definitions and abbreviations are to be used for the interpretation of the claims and the specification. As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but can include other elements not expressly listed or inherent to such composition, mixture, process, method, article, or apparatus.

Additionally, the term "exemplary" is used herein to mean "serving as an example, instance or illustration." Any embodiment or design described herein as "exemplary" is not necessarily to be construed as preferred or advantageous over other embodiments or designs. The terms "at least one" and "one or more" may be understood to include any integer number greater than or equal to one, i.e. one, two, three, four, etc. The terms "a plurality" may be understood to include any integer number greater than or equal to two, i.e. two, three, four, five, etc. The term "connection" may include both an indirect "connection" and a direct "connection."

The terms "about," "substantially," "approximately," and variations thereof, are intended to include the degree of error associated with measurement of the particular quantity based upon the equipment available at the time of filing the application. For example, "about" can include a range of ±8% or 5%, or 2% of a given value.

For the sake of brevity, conventional techniques related to making and using aspects of the invention may or may not be described in detail herein. In particular, various aspects of computing systems and specific computer programs to implement the various technical features described herein are well known. Accordingly, in the interest of brevity, many conventional implementation details are only mentioned briefly herein or are omitted entirely without providing the well-known system and/or process details.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instruction by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope of the described embodiments. The terminology used herein was chosen to best explain the principles of the embodiments, the practical application or technical improvement over technologies found in the marketplace, or to enable others of ordinary skill in the art to understand the embodiments described herein.

What is claimed is:

1. A computer-implemented method comprising:
    determining, via a processing system, a medical condition of an individual based at least in part on a personal identifier associated with the individual, the medical condition further being determined by performing natural language processing of medical information associated with the individual, wherein the medical information is retrieved from a medical database, wherein the personal identifier associated with the individual is determined from a form of electronic payment associated with the individual, wherein the personal identifier is pre-registered with the processing system, and wherein the personal identifier is linked to the medical information stored on the medical database;
    determining, via the processing system, a restriction associated with the medical condition of the individual, wherein the restriction is one of a plurality of restrictions associated with the individual, wherein the individual ranks the plurality of restrictions according to a severity of at least one of the plurality of restrictions, wherein the plurality of restrictions is retrieved from the medical database, and wherein the plurality of restrictions are linked to the medical information stored on the medical database;
    determining, via the processing system, characteristics of a plurality of items based on an identification of the plurality of items scanned by a scanning system and item features retrieved from an item database, wherein the item features are linked to the medical information stored on the medical database;
    comparing, via the processing system, the characteristics of the plurality of items to the restriction associated with the medical condition of the individual; and
    responsive to determining that at least one of the characteristics of the plurality of items violates the restriction associated with the medical condition of the individual, declining, via the processing system, electronic payments associated with the individual, for an item of the plurality of items that includes the at least one of the characteristics of the plurality of items that violates the restriction.

2. The computer-implemented method of claim 1, further comprising:
    responsive to determining that at least one of the characteristics of the plurality of items violates the one or more restrictions associated with the medical condition of the individual, notifying the individual of the violation.

3. The computer-implemented method of claim 1, further comprising:
    responsive to determining that at least one of the characteristics of the plurality of items violates the one or more restrictions associated with the medical condition of the individual, recommending a substitute item in lieu of the item associated with the violation.

4. The computer-implemented method of claim 1, further comprising:
    prior to obtaining the characteristics of the plurality of items, receiving an identification of each of the plurality of items, wherein obtaining the characteristics is based at least in part on the identification of each of the plurality of items; and
    prior to obtaining the medical condition of the individual, receiving, by the processing system, the personal identifier associated with the individual.

5. The computer-implemented method of claim 1, wherein the natural language processing is rule-based natural language processing.

6. The computer-implemented method of claim 1, wherein the natural language processing is machine learning-based natural language processing.

7. A system comprising:
    a memory comprising computer readable instructions;
    a scanning system; and
    a processing device for executing the computer readable instructions, the computer readable instructions controlling the processing device to perform operations comprising:
        determining, via the processing device, a medical condition of an individual based at least in part on a personal identifier associated with the individual, the medical condition further being determined by performing natural language processing of medical information associated with the individual, wherein the medical information is retrieved from a medical database, wherein the personal identifier associated with the individual is determined from a form of electronic payment associated with the individual, wherein the personal identifier is pre-registered with the processing device, and wherein the personal identifier is linked to the medical information stored on the medical database;
        determining, via the processing device, a restriction associated with the medical condition of the individual, wherein the restriction is one of a plurality of restrictions associated with the individual, wherein the individual ranks the plurality of restrictions according to a severity of at least one of the plurality of restrictions, wherein the plurality of restrictions is retrieved from the medical database, and wherein the plurality of restrictions are linked to the medical information stored on the medical database;
        determining, via the processing device, characteristics of a plurality of items based on an identification of the plurality of items scanned by the scanning system and item features retrieved from an item database, wherein the item features are linked to the medical information stored on the medical database;
        comparing, via the processing device, the characteristics of the plurality of items to a restriction associated with the medical condition of the individual; and
        responsive to determining that at least one of the characteristics of the plurality of items violates the restriction associated with the medical condition of the individual, declining, via the processing device, electronic payments associated with the individual, for an item of the plurality of items that includes the at least one of the characteristics of the plurality of items that violates the restriction.

8. The system of claim 7, the operations further comprising:
responsive to determining that at least one of the characteristics of the plurality of items violates the one or more restrictions associated with the medical condition of the individual, notifying the individual of the violation.

9. The system of claim 7, the operations further comprising:
responsive to determining that at least one of the characteristics of the plurality of items violates the one or more restrictions associated with the medical condition of the individual, recommending a substitute item in lieu of the item associated with the violation.

10. The system of claim 7, the operations further comprising:
prior to obtaining the characteristics of the plurality of items, receiving an identification of each of the plurality of items, wherein obtaining the characteristics is based at least in part on the identification of each of the plurality of items; and
prior to obtaining the medical condition of the individual, receiving, by the processing device, the personal identifier associated with the individual.

11. The system of claim 7, wherein the natural language processing is rule-based natural language processing.

12. The system of claim 7, wherein the natural language processing is machine learning-based natural language processing.

13. A computer program product comprising a computer readable storage medium having program instructions embodied therewith, the program instructions executable by a processor to cause the processor to perform operations comprising:
determining, via a processing system, a medical condition of an individual based at least in part on a personal identifier associated with the individual, the medical condition further being determined by performing natural language processing of medical information associated with the individual, wherein the medical information is retrieved from a medical database, wherein the personal identifier associated with the individual is determined from a form of electronic payment associated with the individual, wherein the personal identifier is pre-registered with the processing system, and wherein the personal identifier is linked to the medical information stored on the medical database;
determining, via the processing system, a restriction associated with the medical condition of the individual, wherein the restriction is one of a plurality of restrictions associated with the individual, wherein the individual ranks the plurality of restrictions according to a severity of at least one of the plurality of restrictions, wherein the plurality of restrictions is retrieved from the medical database, and wherein the plurality of restrictions are linked to the medical information stored on the medical database;
determining, via the processing system, characteristics of a plurality of items based on an identification of the plurality of items scanned by a scanning system and item features retrieved from an item database, wherein the item features are linked to the medical information stored on the medical database;
comparing, via the processing system, the characteristics of the plurality of items to the restriction associated with the medical condition of the individual; and
responsive to determining that at least one of the characteristics of the plurality of items violates the restriction associated with the medical condition of the individual, declining, via the processing system, electronic payments associated with the individual, for an item of the plurality of items that includes the at least one of the characteristics of the plurality of items that violates the restriction.

14. The computer program product of claim 13, the operations further comprising:
responsive to determining that at least one of the characteristics of the plurality of items violates the one or more restrictions associated with the medical condition of the individual, notifying the individual of the violation.

15. The computer program product of claim 13, the operations further comprising:
responsive to determining that at least one of the characteristics of the plurality of items violates the one or more restrictions associated with the medical condition of the individual, recommending a substitute item in lieu of the item associated with the violation.

16. The computer program product of claim 13, the operations further comprising:
prior to obtaining the characteristics of the plurality of items, receiving an identification of each of the plurality of items, wherein obtaining the characteristics is based at least in part on the identification of each of the plurality of items; and
prior to obtaining the medical condition of the individual, receiving, by the processing system, the personal identifier associated with the individual.

17. The computer-implemented method of claim 1, wherein the medical condition includes a nut allergy, high blood pressure, or dietary restrictions; and
wherein the characteristics of a plurality of items includes a product identifier, an ingredient, a serving size, nutritional information, a manufacturing date, or an expiration date, of the item.

18. The computer-implemented method of claim 17, further comprising:
generating a message that indicates the restriction due to the item; and
transferring the message to a user device.

19. The system of claim 7, wherein the medical condition includes a nut allergy, high blood pressure, or dietary restrictions; and
wherein the characteristics of a plurality of items includes a product identifier, an ingredient, a serving size, nutritional information, a manufacturing date, or an expiration date, of the item.

20. A computer program product of claim 13, wherein the medical condition includes a nut allergy, high blood pressure, or dietary restrictions; and
wherein the characteristics of a plurality of items includes a product identifier, an ingredient, a serving size, nutritional information, a manufacturing date, or an expiration date, of the item.

* * * * *